Figures 1, 2, 3:
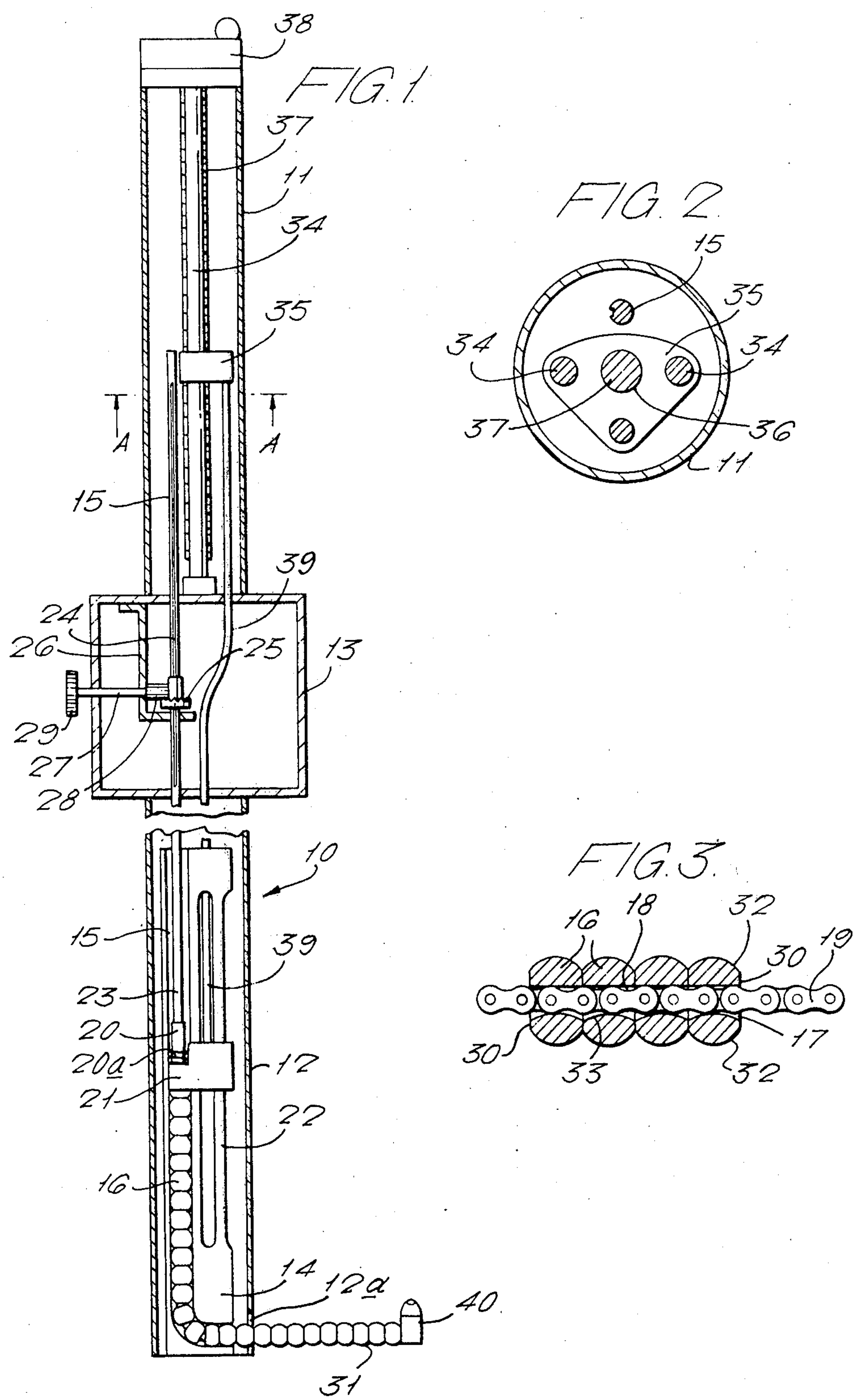

73-633 SR

OR 3,990,301

X 31106

United States Patent [19]

Smith

[11] 3,990,301

[45] Nov. 9, 1976

[54] INSPECTION DEVICE

[75] Inventor: Athol Smith, Derby, England

[73] Assignee: Rolls-Royce (1971) Limited, London, England

[22] Filed: Oct. 31, 1975

[21] Appl. No.: 627,788

[30] Foreign Application Priority Data

Nov. 28, 1974 United Kingdom 51527/74

[52] U.S. Cl. 73/67.8 S; 74/242.8; 74/501 R; 324/37

[51] Int. Cl.[2] G01N 29/00

[58] Field of Search 73/67.8 S, 67.8 R, 71.5 US; 324/37 R, 40 R; 74/501 R, 242.8

[56] References Cited

UNITED STATES PATENTS

| | | | |
|---|---|---|---|
| 3,096,962 | 7/1963 | Meijs | 74/501 R |
| 3,546,961 | 12/1970 | Marton | 74/501 R |
| 3,621,708 | 11/1971 | Regas | 73/67.8 S |
| 3,831,084 | 8/1974 | Scalese et al. | 324/40 R |

*Primary Examiner*—Richard C. Queisser
*Assistant Examiner*—Stephen A. Kreitman
*Attorney, Agent, or Firm*—Cushman, Darby & Cushman

[57] ABSTRACT

An inspection device for inspecting regions of workpieces which are inaccessible to conventional inspection devices. The device comprises a body from which a plurality of abutting members are adapted to extend. The abutting members are interconnected by a tensionable roller chain which is adapted to maintain the abutting members in compression, thereby forming a substantially rigid column which may be provided an inspection probe. The thus formed rigid column may be disposed in angular disposition to the device body.

8 Claims, 5 Drawing Figures

X rotation around vessel 31106

S 38
37
11
34
35
A
A
15
39
24
26
25
13
29
27
28
10
15
39
23
20
20a
21
12
22
16
14
12a
40
31

15
35
34
34
37
36
11

16
18
32
30
19
30
33
32
17

38
44
35
11
29
13
12
46
45
41
43
40
42

INSPECTION DEVICE

This invention relates to an inspection device.

It is sometimes necessary to inspect regions of workpieces which are inaccessible to conventional inspection devices. A particularly inaccesible type of region is that which can only be reached along a path which has two adjacent portions angularly disposed with respect to each other. An example of an inaccessibly region of this type may be found in the rotor drum of a gas turbine engine. It is sometimes necessary to weld together the peripheries of the discs which usually make up a gas turbine engine rotor drum. This results in a rotor drum in which some radial faces of discs are very difficult to inspect; the only access to these faces being via a path which runs along the longitudinal axis of the rotor drum and which is consequently perpendicular to the faces.

The present invention provides an inspection device which may be used for the inspection of such inaccessible regions.

According to the present invention, an inspection device comprises a support means, a series of abutting members adapted to extend from said support means, flexible tensionable means adapted in operation to hold said abutting members in compression to form a substantially rigid column, means adapted to maintain said substantially rigid column in angular disposition to said support means, and at least one inspection probe mounted on said substantially rigid column.

Said series of abutting members preferably comprise part of a greater series of abutting members, the remainder of which are located within said support means, means being provided to cause a greater or lesser proportion of the complete series to extend from said support means.

Said means adapted to maintain said substantially rigid column in angular disposition to said support means may comprise a guide channel provided in said support means, said guide channel being adapted to receive at least part of said series of abutting members and divide and maintain that part into two extents which are angularly disposed with respect to each other.

Said abutting members are each preferably provided with a passage so disposed that said passages together define an elongate passageway adapted to contain said at least one tensionable flexible means.

Each of said abutting members is preferably provided with flat faces adapted to engage with the flat faces of adjacent abutting members.

Said abutting members may be provided with means adapted to prevent relative rotation between said abutting members.

Preferably means are provided for adjusting the tension in said at least one tensionable flexible means.

Said at least one tensionable flexible means may comprise a roller chain.

The invention will be described, merely by way of example, with reference to the accompanying drawings in which:-

Figure 4:
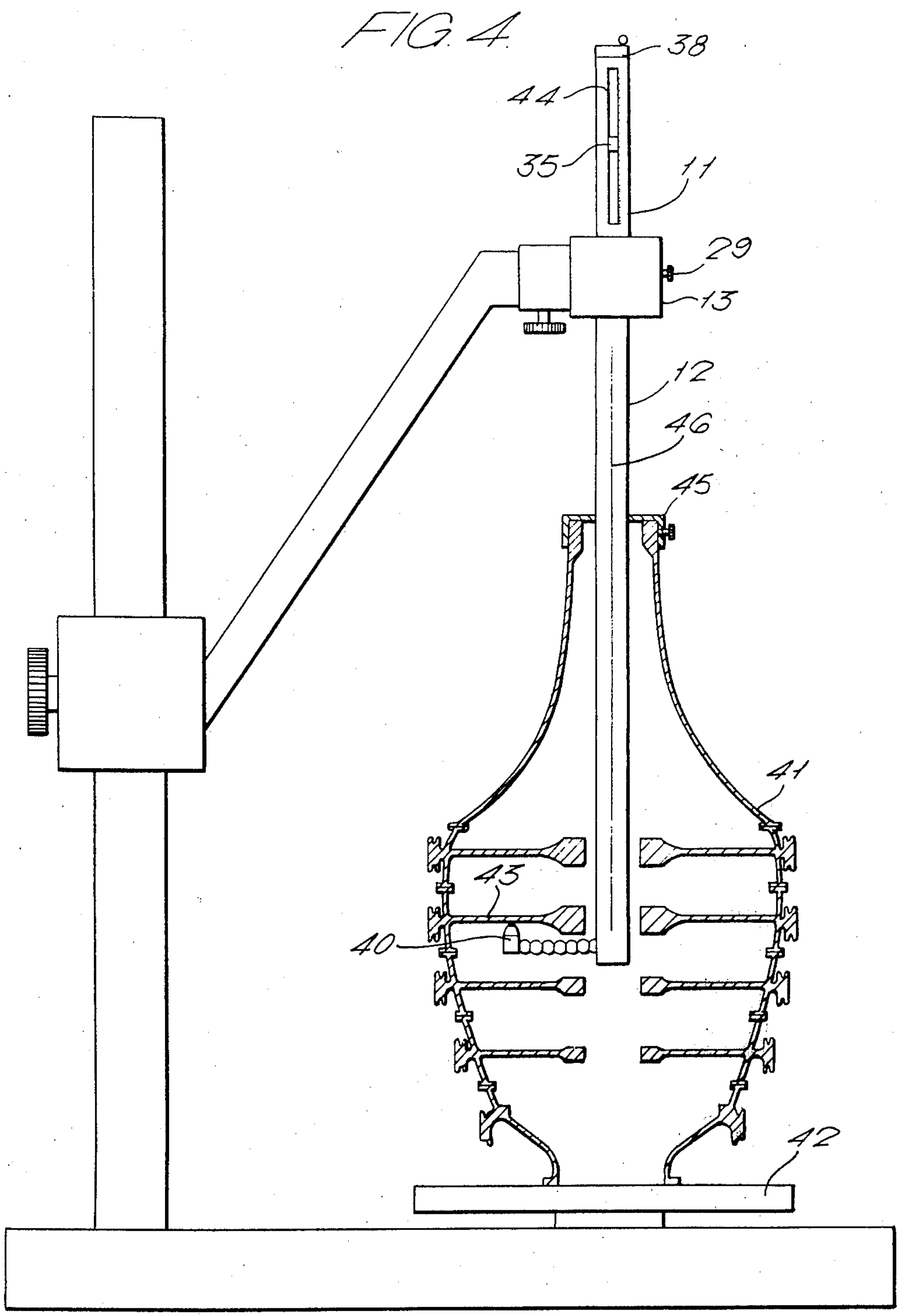
Figure 5:
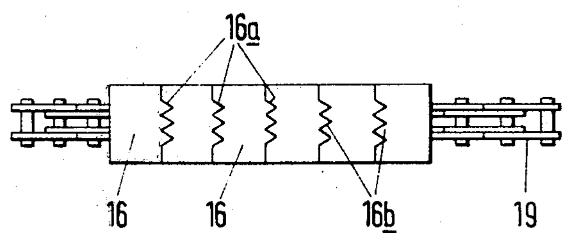

FIG. 1 is a partly sectioned side view of an inspection device in accordance with the present invention, FIG. 2 is an enlarged sectioned plan view of the inspection device shown in FIG. 1 when viewed in the direction indicated by the line A-A, FIG. 3 is an enlarged sectioned side view of a part of the inspection device shown in FIG. 1, FIG. 4 is a side view of the inspection device shown in FIG. 1 inspecting the welded compressor drum of a gas turbine engine and, FIG. 5 is a plan view of a modified part of the inspection device, the view disclosing one form of means for preventing relative rotation between the support members.

With reference to FIG. 1 an inspection device generally indicated at 10 comprises two elongate tubular members 11 and 12 which are interconnected by a box-like member 13. In the interests of clarity, a portion of the length of the tubular member 12 has been omitted.

In the interior of the tubular member 12 there is mounted a guide 14 which extends along a major portion of the length of the tubular member 12. The guide 14 is provided with a channel 15 throughout substantially the whole of its length; the channel 15 being arranged to be parallel with the longitudinal axis of the tubular member 12 before curving into a direction substantially perpendicular to the longitudinal axis at that end of the tubular member 12 remote from the box-like member 13.

The channel 15 is adapted to receive at least some of a plurality of similar substantially rectangular support members 16 which are arranged in series abutting relationship. The abutting surfaces of the support members 16 are flat. However, if for some reason it is essential that there is no relative rotational movement between the support members 16, the abutting surfaces could be provided, for instance, with teeth **16*a* adapted to interengage with teeth 16*b* on adjacent support members 16 as shown in FIG. 5. Each support member 16, four of which can be more easily seen in FIG. 3, is provided with an internal passage 17. The passages 17 are so disposed in the support members 17 that together they define a single passageway 18 which extends throughout the whole length of the series of support members. The passageway 18 is adapted to receive a roller chain 19 which extends through all of the support members 16 and is attached to that final support member in the series which is remote from the box-like member 13. The other end of the roller chain 19 is attached to a screw threaded bolt (not shown) which in turn locates in a threaded sleeve 20**.

The screw threaded bolt is adapted to pass through a hole which is provided in a saddle 21 mounted for translation on a slide 22 provided on the guide 14. The hole in the saddle 21 is arranged to be substantially parallel with the longitudinal axis of the tubular member 12 and is of such diameter that only the screw threaded bolt may pass freely through it. The screw threaded bolt is located in the hole in the saddle 21 with the threaded sleeve 20 and the support member 16 to which the threaded bolt is attached positioned on opposite sides of the saddle 21. A helical compression spring **20*a* is interposed between the threaded sleeve 20 and the saddle 21. The threaded sleeve 20 is attached to an actuating rod 23 which extends through the tubular member 12, and the box-like member 13 into the tubular member 11. That portion of the actuating rod 23 which passes through the box-like member 13 and the tubular member 11 is provided with a keyway 24 to which is keyed a contrate gear wheel 25. The contrate gear wheel 25 is retained in position on the actuating rod 23 within the box-like member 13 by means of support bracket 26 which is located inside the box-like member 13. The bracket 26** also supports a shaft 27 on which is mounted a pinion 28 adapted to drivingly engage with the contrate gear wheel 25. The shaft 27 protrudes beyond the exterior wall of the box-like member 13 where it terminates in a finger wheel 29. It will be seen therefore that rotation of the finger wheel 29 results in the rotation of the actuating rod 23 and hence the threaded sleeve 20 which in turn results in the tensioning of the roller chain 19 and hence the urging into compression of the support member 16.

Each of the support members 16 is provided with flat faces 30 which are arranged to be perpendicular to the longitudinal axis of the internal passage 17 in the member. The flat faces 30 are adapted to abut the flat faces 30 of adjacent support members 16 so that when support members 16 are held in compression as a result of the tensioning of the roller chain 19, they tend to be drawn into a substantially rigid column. However, the channel 15 in which the support members 16 are located is not linear but substantially L-shaped. Consequently the support members 16 are constrained to follow its L-shape. Some of the support members 16 are adapted to protrude beyond that part of the channel 15 which is perpendicular to the longitudinal axis of the tubular member 12. A hole 12*a* is provided in the tubular member 12 opposite the lower end of the channel 15 so that those support members 16 not contained within the channel 15 may protrude beyond the outer wall of tubular member 12.

When the roller chain 19 is tensioned, those support members 16 protruding beyond the channel 15 form themselves into a free, substantially rigid column 31 which is perpendicular to the longitudinal axis of the tubular member 12. The actual free length of the column 31 is adjusted by appropriately translating the saddle 21 along the slide 22.

The surfaces 32 of the support members 16 which contact the curved surfaces of the channel 15 are each convex in a single plane so as to ensure free passage of the support members over the curved surfaces of the channel 15. In addition, the surfaces 33 of the internal passages 17 in the support members 16 upon which the roller chain 19 bears in the region of curved surfaces of the channel 15 are also convex in a single plane so as to present a substantially continuous curved surface to the roller chain 19.

The interior of the tubular member 11 is provided with two parallel slides 34 which are also arranged to be parallel with the longitudinal axis of the tubular member 11 and on which are mounted a carriage 35. The carriage 35 is provided with a threaded hole 36 which is adapted to cooperate in driving engagement with a lead screw 37 positioned between and arranged to be parallel with the slides 34. The lead screw 37 extends beyond the end of the tubular member 11 remote from the box-like member 13 before terminating in a hand wheel 38. Thus rotation of the hand wheel 38, and consequently the lead screw 37, results in the translation of the carriage 35 along the slides 34. The carriage 35 is attached, by means of an elongate cranked actuating rod 39 passing through the box-like member 13, to the saddle 21. Thus translation of the carriage 35 by means of the hand wheel 38 results in the corresponding translation of the saddle 21 and consequently the plurality of support members 16.

The free end of the column of support members 31 is provided with an inspection probe 40 which may be of any convenient type e.g. and eddy current detector.

During the inspection of a component such as the welded compressor drum of a gas turbine engine compressor, the compressor drum 41, which can be seen in FIG. 4, is positioned on a turntable 42 so that the longitudinal axis of the compressor drum 41 is coaxial with the axis of rotation of the turntable 42. The inspection device 10 is then inserted into the compressor drum 41 and positioned so that its longitudinal axis is also coaxial with the axis of rotation of the turntable. The inspection device 10 is then lowered into the compressor drum 41 until the inspection probe 40 is level with the disc 43 under inspection. Tensioning of the roller chain 19 by means of the finger wheel 29 follows before the column of support members 31 is wound out by means of the hand wheel 38 to the required distance. The carriage 35 is visible through a graduated window 44 provided in the tubular member 11 so that the actual distance that the column of support members 31 is wound out may be monitored. The turntable 42 is then rotated whilst the signals from the inspection probe 40 are examined.

An apertured cap 45 is provided on that end of the compressor drum 41 through which the inspection device 10 is inserted is angularly graduated for co-operation with a reference line 46 provided on the outer surface of the tubular member 12. As a result the angular disposition of the column of support members 31 may be continuously monitored. Consequently if a fault in the disc 43 is detected by the inspection probe 40, its actual position on the disc 43 may be readily ascertained by reference to the length and angular disposition of the column of support members 31. An inspection survey of virtually the whole of the face of the disc 43 may be effected by varying the length of the column of support members 31 after each complete revolution of the turntable 42.

Although the present invention has been described with reference to an inspection device provided with a roller chain, it will be appreciated that other alternative flexible tensionable means could be used. For instance, provided that means were provided to prevent the relative rotation of the support members 16, the roller chain 19 could be replaced by a cable.

In order to aid the exact positioning of the inspection probe 40, mirrors may be provided on the inspection probe 40, and on the outer ends of the tubular members 11 and 12 so that the probe 40 may be viewed in operation from the outer end of the tubular member 11. Light may be supplied to the probe 40 by means of fibre optics so that the operation of the probe 40 in a dark environment may be observed.

I claim:

1. An inspection device comprising housing means, a series of abutting members adapted to extend from said housing means, flexible means interconnecting said abutting members, means adapted in operation to tension said flexible means so that said abutting members are held in compression to form a substantially rigid column, means adapted to maintain said substantially rigid column in angular disposition to said housing means and at least one inspection probe mounted on said substantially rigid column.

2. An inspection device as claimed in claim 1 wherein said abutting members comprise part of a greater series of abutting members, the remainder of which are located within said housing means, means being provided to cause a greater or lesser proportion of the complete series to extend from said housing means.

3. An inspection device as claimed in claim 1 wherein said means adapted to maintain said substantially rigid column in angular disposition to said housing means comprises a guide channel provided in said housing means, said guide channel being adapted to receive at least part of said series of abutting members and divide and maintain that part into two extents which are angularly disposed with respect to each other.

4. An inspection device as claimed in claim 1 wherein said abutting members are each provided with a passage so disposed that together they define an elongate passageway adapted to contain said flexible means.

5. An inspection device as claimed in claim 1 wherein each of said abutting members is provided with flat faces adapted to engage with the flat faces of adjacent abutting members.

6. An inspection device as claimed in claim 1 wherein said abutting members are provided with means adapted to prevent relative rotation between said abutting members.

7. An inspection device as claimed in claim 1 wherein means are provided for adjusting the tension in said flexible means.

8. An inspection device as claimed in claim 1 wherein said flexible means comprises a roller chain.

* * * * *